United States Patent [19]

Saotome

[11] Patent Number: 4,910,250

[45] Date of Patent: Mar. 20, 1990

[54] AQUEOUS COMPOSITION, METHOD OF PRODUCING A WATER ABSORBENT POLYMER

[75] Inventor: Kazuo Saotome, Tokyo, Japan

[73] Assignee: Hayashikane Shipbuilding & Engineering Co., Ltd., Japan

[21] Appl. No.: 287,521

[22] Filed: Dec. 19, 1988

Related U.S. Application Data

[63] Continuation of Ser. No. 876,539, Jun. 20, 1986, abandoned.

[30] Foreign Application Priority Data

Jun. 22, 1985 [JP] Japan ................. 60-136653
Feb. 7, 1986 [JP] Japan ................. 61-26625

[51] Int. Cl.$^4$ ............................. C08L 31/00
[52] U.S. Cl. ......................... 524/556; 525/387
[58] Field of Search ................. 524/556; 525/387

[56] References Cited

U.S. PATENT DOCUMENTS

| | | | |
|---|---|---|---|
| 4,066,584 | 1/1978 | Allen et al. | 524/556 |
| 4,132,695 | 1/1979 | Burkholder | 524/556 |
| 4,497,930 | 2/1985 | Yamasaki | 524/556 |
| 4,524,186 | 6/1985 | Nagase | 525/387 |
| 4,587,308 | 5/1986 | Makita et al. | 525/387 |

FOREIGN PATENT DOCUMENTS 1080872  7/1980  Canada ..................... 524/556

*Primary Examiner*—Joseph L. Schofer
*Assistant Examiner*—J. M. Reddick
*Attorney, Agent, or Firm*—Sprung Horn Kramer & Woods

[57] ABSTRACT

An aqueous composition of an acrylic polymer to which a water soluble peroxide radical initiator has been added, said initiator being adapted to decompose at a temperature of from about 40° C. to about 180° C. and act on the polymer to crosslink the same. Using the aqueous composition, a water absorbent crosslinked polymer and a water absorbent polymer-coated article can be produced through simplified processes. The water absorbent crosslinked polymer exhibits excellent water absorbing and swelling properties so that it can be advantageously utilized for the production of wet absorbent articles such as disposable diaper, sanitary napkin or the like. The water absorbent polymer-coated article is excellent in water absorption properties and can be used safely for the purposes as mentioned above.

16 Claims, No Drawings

AQUEOUS COMPOSITION, METHOD OF PRODUCING A WATER ABSORBENT POLYMER

This application is a continuation of application Ser. No. 876,539, filed June 20, 1986, now abandoned.

This invention relates to an aqueous composition, a method of producing a water absorbent polymer, a water absorbent polymer-coated article and a method of producing the same. More particularly, this invention is concerned, in one aspect, with an aqueous composition of an acrylic polymer containing a peroxide radical initiator which is adapted to decompose at a temperature of from about 40° to about 180° C. and act on the polymer to crosslink the same. This composition can be advantageously utilized to produce a highly water absorbent polymer, and a highly water absorbent polymer-coated article. Therefore, in another aspect, the present invention is concerned with an improved method of producing an advantageous water absorbent polymer in which the above-mentioned aqueous composition is heated, and, in further aspects, concerned with a highly water absorbent polymer-coated article and with an improved method of producing the same in which the aqueous composition is applied to a substrate, and heated.

Basically, there are three methods known in the art to produce a water absorbent polymer-coated or impregnated article such as a disposable diaper, a sanitary napkin, a surgical pad, a surgical sheet, a paper towel or the like. That is, according to method A, a powdery water absorbent crosslinked polymer having acrylic acid monomeric units as a major component, which can absorb water, urine, menstrual blood or the like in an amount of several hundred times the weight of the polymer, is spread over a substrate such as paper, nonwoven fabric or the like, and steamed to effect swelling of the polymer, followed by pressing and drying thereby to cause the polymer to adhere to the substrate. In this connection, U.S. Pat. Nos. 3,669,103 and 3,810,468 teach that a water soluble polymer produced from a monomeric component such as acrylic acid and acrylamide exhibits a high degree of water absorbency when crosslinking of the polymer molecules is effected, and that crosslinking may be effected, for example, by conducting copolymerization with a bifunctional monomer such as N,N'-methylenebisacrylamide. According to method B, a substrate such as fibrous cellulosic material is subjected to surface treatment such as carboxymethylation to render the substrate water absorbent. According to method C, a solution of a water soluble polymer is applied onto a substrate, and the resulting water soluble polymer-applied substrate is subjected to heat treatment in the presence of a crosslinking agent generally during the drying step to insolubilize the water soluble polymer, thereby imparting a water absorbency thereto.

With respect to method A, it has a drawback that due to the difference in properties such as specific gravity and configuration between the acrylic polymer and the fibrous substrate, the powder of the water absorbent acrylic polymer is removed from the fibrous substrate and distributed unevenly by the vibration occurring during the transportation of the product, etc. Moreover, with respect to method A, there occurs a trouble that a hydrogel formed as a result of water absorption of the water absorbent polymer is separated from the fibrous substrate and comes to direct contact with the skin of a person carrying the product to give an uncomfortable feeling to the person. Moreover, the production of the water absorbent crosslinked acrylic polymer to be employed in method A is accompanied by following problem. To produce a crosslinked acrylic polymer, according to the conventional method, a radical initiator is added to an aqueous solution containing 40% by weight or more of acrylic acid netralized with an alkali metal hydroxide and the resulting mixture is heated. In that method, there rapidly occurs a polymerization reaction while causing partial crosslinking, so that a partially self-crosslinked acrylic polymer is produced. After the initiation of the polymerization reaction, the viscosity of the aqueous solution increases and a gel is formed with the progress of spontaneous crosslinking. While the polymerization reaction is accelerated due to the elevation of the temperature which is attributed to the heat of reaction, evaporation of the steam out of the reaction system is hindered due to the increased viscosity and the gelation of the mixture. As a result, removal of the heat of reaction becomes difficult, and the reaction proceeds uncontrollably with the formation of a popcorn-like material. Especially when the reaction system becomes a gel, generally known "gel effect" occurs to further increase the reaction rate, thereby causing controlling of the polymerization reaction to be more difficult. To obviate such a difficulty, there have been proposed various polymerization methods. For example, it has been proposed to employ a redox system to initiate radical polymerization since the above-mentioned spontaneous crosslinking can be prevented by effecting polymerization under mild conditions at a low temperature. For this method, a continuous polymerization process is feasible. However, this redox system method is disadvantageous because in this method the polymerization reaction requires a prolonged reaction time and a complicated polymerization apparatus, and because in this method the concentration of the aqueous reaction solution is to be kept low to ensure controlling of the heat of polymerization. Therefore, in this method, reduction of the manufacturing cost cannot be expected. Further, a reverse phase suspension polymerization method has been proposed in which polymerization is effected in a dispersion having fine particles of the aqueous reaction solution dispersed in a hydrocarbon solvent. With respect to this method, reference may be made to, for example, U.S. Pat. No. 4,093,776. In this method, it is possible to polymerize acrylic acid in a high concentration aqueous solution. However, this method is disadvantageous because in this method a large amount of a hydrocarbon solvent must be used and a countermeasure against possible fire is required, thereby inevitably leading to an increase in manufacturing cost. Further, in this method, it is difficult to practice a continuous process.

With respect to method B, U.S. Pat. No. 3,005,456 discloses a method in which carboxymethylation of a fibrous cellulose is effected to an extent that solubilization of the cellulose does not occur. According to this method, however, a fibrous product having a high degree of water absorbency cannot be obtained. Further, this method is disadvantageous from the economical point of view, because the carboxymethylation is effected by reacting the cellulose with chloroacetic acid, which is an expensive chemical, in a propanol solution. On the other hand, the method as disclosed in Japanese patent application laid-open specification No. 51-144476/1976 in which absorbent polymer segments are grafted to a fibrous carboxymethyl cellulose may produce a water absorbent fibrous product improved in water absorbency, but inevitably leads to an increase in cost when the method is practiced on a commercial scale because expensive apparatuses and time-consuming operations are required.

With respect to method C, reference may be made to, for example, Japanese patent application laid-open specification No. 50-82143/1975 (priority was claimed on the basis of U.S. patent application Ser. No. 371,909 filed on June 20, 1973), Japanese patent application laid-open specification No. 55-84304/1980 and Japanese patent application laid-open specification No. 58-84804/1983. As disclosed in Japanese patent application laid-open specification No. 50-82143/1975, a water swellable film or coated article is obtained by a method in which a film or coated article is produced from an aqueous solution containing a polymeric electrolyte having carboxylate groups such as sodium polyacrylate and a water soluble crosslinking agent which is capable of reacting with carboxylate groups, and then the film or coated article is heated thereby to effect crosslinking of the polymer. As suitable crosslinking agents, there have been mentioned a polyhaloalkanol, a haloepoxyalkane, a polyglycidyl ether, an amphoteric sulfonium salt, a bisphenol-A-epichlorohydrine type epoxy resin and the like. Japanese patent application laid-open specification No. 55-84304/1980 discloses crosslinking of polymers which is effected by esterification reaction between a polyfunctional alcohol and the carboxyl groups of a polymer. These methods have the following drawback. That is, according to these methods, crosslinking of the polymer is effected by the reactions between the carboxyl or carboxylate groups of the polymer and the functional group for example a hydroxyl group, of the crosslkinking agent. Such reaction must generally be conducted at a high temperature for prolonged period of time. This is disadvantageous from the viewpoint of avoiding the decomposition of the polymer. This is also disadvantageous from the viewpoint of production efficiency. Moreover, according to these methods, it is difficult to attain a desirable degree of crosslinking. In the method of Japanese patent application laid-open specification No. 58-84804/1983 the aqueous solution of the polymer has a high viscosity and therefore is difficult to be uniformly permeated into the fibrous material unless the aqueous solution is highly diluted to a solution having an extremely low concentration. Moreover, the method is disadvantageous in that it is difficult to control the crosslinking reaction and to attain uniform crosslinking and density of crosslinking, thereby leading to insufficient absorbency.

In most cases, fibrous products containing a water absorbent polymer are used for the production of disposable articles. Hence, low cost is the prime requirement for such absorbent fibrous products. However, the efforts for providing low-cost water absorbent fibrous products have not been satisfactorily successful.

As is apparent from the foregoing, all of the prior art methods and products are advantageous in some points but disadvantageous in other points.

Noting the advantages of method C as described above, the inventor has made extensive and intensive studies to resolve the disadvantages of the method. As a result, it has unexpectedly been found that an aqueous composition comprising water, an acrylic polymer dissolved or swollen in the water and a peroxide radical initiator substantially dissolved in the water can be advantageously utilized to produce an advantageous water absorbent crosslinked polymer and an advantageous water absorbent polymer-coated article. Based on this unexpected finding, the present invention has been completed.

It is, therefore, an object of the present invention to provide a novel aqueous composition which can be advantageously utilized to produce a water absorbent crosslinked polymer and a water absorbent polymer-coated article.

It is another object of the present invention to provide an improved method of producing a water absorbent crosslinked polymer which can absorb water, urine, menstrual blood or the like in an amount of several hundred times the weight of the polymer.

It is a further object of the present invention to provide an improved method of producing a water absorbent polymer-coated article.

It is still a further object of the present invention to provide a novel water absorbent polymer-coated article which is advantageously uniform with respect to water absorption and which is safe to humans.

The foregoing and other objects, features and advantages of the present invention will be apparent to those skilled in the art from the following detailed description and appended claims.

In one aspect of the present invention, there is provided an aqueous composition comprising water, a polymer dissolved or swollen in said water, said polymer having at least 70% by weight, based on the total weight of said polymer, of acrylic acid monomeric units, 60 to 90% of the carboxyl groups of said monomeric units being in the form of an alkali metal salt, and a peroxide radical initiator substantially dissolved in said water, said initiator being adapted to decompose at a temperature of from about 40° to about 180° C. and act on said polymer to crosslink said polymer and being present in an amount sufficient to crosslink said polymer, said water being present in an amount of at least about 10% based on said composition.

In the present invention, the aqueous composition is prepared by adding a water soluble peroxide radical initiator to an aqueous mixture comprised of water and a polymer dissolved or swollen in the water. The polymer has at least 70% by weight, based on the total weight of the polymer, of acrylic acid monomeric units, 60 to 90% of the carboxyl groups of which are in the form of an alkali metal salt. A polyacrylic acid salt is an example of the suitable polymers. The other suitable polymers may be prepared by copolymerizing acrylic acid with a comonomer as a minor component such as methacrylic acid, maleic anhydride, fumaric acid, acrylamide, and methacrylamide or by effecting graft copolymerization of acrylic acid onto a water soluble polymer such as starch.

The above-defined aqueous mixture may be prepared according to customary procedures. For example, it may be prepared as follows. First, a 10 to 40% by weight aqueous monomeric component solution is prepared by dissolving a monomeric component comprising at least 70% by weight of acrylic acid based on the component in water and neutralizing 60 to 90% of the carboxyl groups of the acrylic acid with an alkali metal hydroxide such as sodium hydroxide and potassium hydroxide. Next, a radical initiator such as ammonium persulfate and potassium persulfate is added to the aqueous monomeric component solution in an amount of, generally, from 0.05 to 0.2% by weight based on the monomeric component, and polymerization reaction is effected to obtain an aqueous mixture. It is preferred that polymerization reaction of the monomeric component be effected in an inert atmosphere such as gaseous nitrogen. Polymerization reaction is generally effected at a temperature of from 50° to 100° C. It is however possible to conduct polymerization reaction at room temperature by employing a redox initiator system in which a peroxide radical initiator is used in combination with a reducing agent such as a sulfite salt which promotes decomposition of the peroxide initiator. The polymerization reaction rate and accordingly the polymerization reaction time depend on monomeric component concentration, initiator concentration, reaction temperature and other reaction conditions. Whether the resulting polymer is completely dissolved in the water or obtained in a swollen form depends also on monomeric component concentration, initiator concentration, reaction temperature and other reaction conditions.

A water soluble peroxide radical initiator adapted to decompose at a temperature of from about 40° to about 180° C. and act on the polymer to crosslink the same is added to the above-described aqueous mixture in an amount sufficient to crosslink the polymer to obtain an aqueous composition of the present invention.

The use of an organic peroxide is known in the plastics and rubber industries to effect radical crosslinking of polyethylene, poly(ethylene-co-vinyl acetate), poly-(ethylene-co-propylene) rubber or the like. Such radical crosslinking is effective only for limited kinds of thermoplastic polymers and is not effective for butyl rubber or the like. To perform radical crosslinking of the thermoplastic polymers, an oil soluble organic peroxide is generally employed. Formation of crosslinking proceeds with the progress of decomposition of the peroxide, and is completed within a short period of several minutes. A water soluble peroxide radical initiator lacks compatibility with these polymers and hence cannot be used to effect radical crosslinking thereof. As far as the inventor's knowledge extends, there is no report indicating the use of a water soluble peroxide radical initiator for effecting radical crosslinking of polymers.

The inventor has conceived of preparation of a wet absorbent polymer by effecting radical crosslinking with respect to an aqueous composition of an acrylic polymer to which a water soluble peroxide radical initiator has been added, has studied and has made the following unexpected finding. A detailed study has been made of the aqueous compositions of a polyacrylic acid, 75% of the carboxyl groups of which have been neutralized with caustic soda, containing potassium persulfate in an amount of 2% by weight based on the polymer, which compositions have been caused to have various water contents by effecting concentration under reduced pressure at a temperature at which decomposition of the persulfate substantially does not occur. From the study, it has unexpectedly been found that radical crosslinking of the polymer in the aqueous composition scarcely occurs in the absence of water or at a water content of less than about 10% by weight in the aqueous composition, and that it is preferred for radical crosslinking of the polymer in the aqueous composition that water be present in an amount of greater than 20%, especially 30% by weight but less than 60%, especially 50% by weight based on the composition. This suggests that water functions as a plasticizer, and that in the absence of water or at a water content as low as less than about 10% by weight, polymer molecules tend to be frozen, thereby causing the crosslinking reaction to be hindered.

With respect to polymerization, in the presence of a peroxide radical initiator, of an aqueous solution of a monomeric component comprising at least 70% by weight of acrylic acid, 60 to 90% of the carboxyl groups of which have been neutralized with an alkali metal hydroxide, it may be assumed that when the initiator is added in an amount exceeding that to be consumed in the polymerization reaction and polymerization is effected, a portion of the initiator added remains undecomposed so that the same composition as that of the present invention is obtained. That is, it may be assumed that the composition of the present inveniton is not different from the above-defined composition, because both of them are to comprise water, the same kind of polymer and the same kind of initiator. However, this assumption is wrong for the following reason. When polymerization of such a monomeric component is effected using a peroxide radical initiator in an amount exceeding that to be consumed in the polymerization reaction, spontaneous crosslinking and gelation of the reaction mixture occur, thereby causing control and continuation of the polymerization reaction to be difficult. At the same time, the quality of the resulting polymer is caused to be poor. These are especially apparent when the monomeric component concentration of the aqueous solution is at a high level. Therefore, polymerization of the monomeric component using an initiator in an amount exceeding that to be consumed in the polymerization reaction does not lead to the aqueous composition of the present invention.

As the water soluble peroxide radical initiator to be employed in the present invention, there may be mentioned, for example, persulfate salts such as ammonium persulfate, sodium persulfate and potassium persulfate, inorganic compounds such as hydrogen peroxide and organic compounds such as acetic acid peroxide, succinic acid peroxide and t-butyl peroxymaleic acid. From the viewpoints of the decomposition temperature, crosslinking efficiency and cost of the initiator, ammonium persulfate and potassium persulfate are most preferred. The water soluble peroxide radical initiator is incorporated in the aqueous composition of the present invention in an amount sufficient to crosslink the polymer and in such an amount that the water substantially dissolves the initiator therein. The radical initiator may be incorporated in the aqueous composition of the present invention in an amount of generally from 0.01 to 10% by weight, preferably from 0.1 to 5% by weight, more preferably from 0.5 to 3% by weight based on the polymer. As mentioned above, the radical initiator is substantially dissolved in the aqueous composition of the present invention. The terminology "substantially dissolved" as used herein means that generally the initiator is completely dissolved in the aqueous composition but it may occur that a portion, for example at most about 10%, remains undissolved. When an excess amount of a radical initiator is added so that a large portion of the initiator remains undissolved, the ultimate products become disadvantageously non-uniform with respect to crosslinking and hence water absorbing properties. The radical initiator may be added in the form of powder or an aqueous solution. When the polymer is in a swollen form, uniform dispersion of the initiator may be attained by a kneader or other mechanical means.

The aqueous composition of the present invention can be advantageously utilized to produce a water absorbent crosslinked polymer. Accordingly, in another aspect of the present invention, there is provided a method of producing a water absorbent crosslinked polymer, which comprises the steps of:

(1) providing an aqueous mixture comprised of water and a polymer dissolved or swollen in said water, said polymer having at least 70% by weight, based on the total weight of said polymer, of acrylic acid monomeric units, 60 to 90% of the carboxyl groups of said monomeric units being in the form of an alkali metal salt;

(2) adding a water soluble peroxide radical initiator, said initiator being adapted to decompose at a temperature of from about 40° to about 180° C. and act on said polymer to crosslink said polymer, to said mixture in an amount sufficient to crosslink said polymer and in such an amount that said water substantially dissolves said initiator thereby to obtain an aqueous composition; and (3) heating said aqueous composition at a temperature of from about 40° to about 180° C.

Moreover, the aqueous composition of the present invention can be advantageously utilized to produce a water absorbent polymer-coated article. Accordingly, in a further aspect of the present invention, there is provided a method of producing a water absorbent polymer-coated article, which comprises the steps of:

(1) providing an aqueous mixture comprised of water and a polymer dissolved or swollen in said water, said polymer having at least 70% by weight, based on the total weight of said polymer, of acrylic acid monomeric units, 60 to 90% of the carboxyl groups of said monomeric units being in the form of an alkali metal salt;

(2) adding a water soluble peroxide radical initiator, said initiator being adapted to decompose at a temperature of from about 40° to about 180° C. and act on said polymer to crosslink said polymer, to said mixture in an amount sufficient to crosslink said polymer and in such an amount that said water substantially dissolves said initiator therein thereby to obtain an aqueous composition;

(3) coating or impregnating a substrate with said aqueous composition; and (4) heating the resulting coated or impregnated substrate at a temperature of from about 40° to about 180° C.

As mentioned hereinbefore, radical crosslinking of the acrylic polymer by a water soluble peroxide radical initiator scarcely occurs in the absence of water or at a water content as low as less than about 10% by weight, and water is needed for effective crosslinking of the polymer. When the amount of water in the aqueous mixture is less than such an amount as will cause the aqueous composition to have a water content of at least about 10% by weight, water is added together with a peroxide radical initiator to the aqueous mixture so that the resulting aqueous composition has a water content of at least about 10% by weight. It has been found that radical crosslinking of the acrylic polymer by a water soluble peroxide radical initiator more effectively occurs when water is present in an amount of at least about 20%, especially from about 20% to about 60%, more especially from about 30% to about 50% based on the composition.

To produce a water absorbent crosslinked polymer, the aqueous composition is heated at a temperature of about 40° to about 180° C. When an aqueous composition having a high water content, for example 90% is employed, it is preferred that the composition be concentrated by heating, under reduced pressure, at a temperature, for example, less than about 40° C., at which decomposition of the initiator substantially does not occur, to arrive at a suitable water content of, for example 20% to 60%, thereby enabling effective crosslinking to occur. To attain effective radical crosslinking promptly, it is preferred that use be made of an aqueous mixture comprised of water and a polymer dissolved or swollen in the water, which polymer has at least 70% by weight, based on the total weight of the polymer, of acrylic acid monomeric units, 60 to 90% of the carboxyl groups of which are in the form of an alkali metal salt, and which water is contained in the aqueous mixture in an amount such as will cause the aqueous composition to have a water content of at least about 20%, especially from about 20% to about 60%.

On the other hand, to produce a water absorbent polymer-coated article, a substrate is coated or impregnated with an aqueous composition, followed by heating at a temperature of from 40° to 180° C. To facilitate the coating or impregnation, it is desired that the aqueous composition have a low viscosity, for example about 50 to about 50,000 cps at 25° C. as measured using a Brookfield viscometer. The aqueous composition having a viscosity of about 50 to about 50,000 cps may be prepared by using a high watercontent aqueous mixture, for example, an aqueous mixture comprised of water and a polymer dissolved or swollen in the water, which polymer has at least 70% by weight, based on the total weight of the polymer, of acrylic acid monomeric units, 60 to 90% of the carboxyl groups of which are in the form of an alkali metal salt, and which water is present in an amount of more than about 60%, especially more than about 90% based on the mixture. Further, the aqueous composition having a viscosity of about 50 to about 50,000 cps may also be prepared by adding a volatile organic solvent to the aqueous mixture of the acrylic polymer, which solvent is capable of forming a mixed solvent with water. As a suitable volatile, water soluble solvent, there may be mentioned, for example, an alcohol such as methanol and ethanol and a ketone compound such as acetone and methyl ethyl ketone. Of the above-mentioned solvents, methanol is most preferred. To attain a substantial decrease in the viscosity of the aqueous composition, it is preferred that the solvent be present in an amount of from 0.1 to 5 in terms of the volume ratio of the solvent to water. When an aqueous composition having a water content as high as more than 60% by weight based on the composition, it is generally preferred that the aqueous composition be concentrated by heating, under reduced pressure, at a temperature, for example, less than about 40° C., at which decomposition of the initiator substantially does not occur, to arrive at a suitable water content of, for example 20 to 60%, thereby enabling effective crosslinking to occur.

The kind of the substrate to be coated or impregnated with the aqueous composition of the present invention is not critical, as far as it does not contain any substance which adversely affects formation of a crosslinked polymer coat layer, such as an inorganic salt and a radical inhibitor. The substrate may be porous or non-porous. However, a porous substrate generally finds more applications. As a suitable substrate, there may be mentioned a cotton-like material, paper, non-woven fabric, fabric, felt, mat or the like which is composed of natural fibers such as those of pulp, cotton, rayon and wool or synthetic fibers such as those of a polyolefin, a polyester, a polyamide (nylon) and a polyacrylonitrile. When a porous substrate is employed, coating can be effected deep inside the substrate. Penetration of the aqueous composition can be freely regulated by varying the viscosity and polymer concentration of the aqueous composition. A non-porous, smooth surface substrate can also be used. For example, it can be used for the purpose of dew condensation prevention. The substrate may be coated or impregnated with the aqueous composition of the present invention by means of a sprayer, rolls, a slit extrusion-type coating machine or the like.

Heating of the aqueous composition or the aqueous composition-coated or impregnated substrate to effect crosslinking of the acrylic polymer is conducted at a temperature at which the water soluble peroxide radical initiator is decomposed, which temperature is generally in the range of from about 40° to about 180° C. It is preferred that the above-mentioned heating be conducted at a temperature at which the half life of the decomposition of the peroxide radical initiator is in the range of from about 60 to about 20 seconds. This temperature is, for example, in the range of about 120° to about 130° C. with respect to persulfate salts. In this respect, reference may be made to I. M. Kolthoff and I. K. Miller : J. Am. Chem. Soc., 73, 3056 (1951). It is apparent that these temperatures are also suitable for evaporating water thereby to dry the product. Hence, persulfate salts are suitable radical initiators in the present invention. In this connection, it is to be noted that when an ordinary dryer is employed, the temperature of the aqueous composition is about 5° to 20° C. lower than the temperature of the dryer due to evaporation of water. When a substrate of fibers coated or impregnated with the aqueous composition is heated, rapid evaporation of water occurs. Hence, to effect cross-linking promptly while maintaining an appropriate water content for effecting crosslinking of the polymer, it is preferred that heating be conducted by steam heated to about 130° to about 150° C. The period of time during which heating is continued depends on the kind and amount of the initiator, temperature of the heating, etc. However, it is generally in the range of from about 1 to about 10 minutes.

In the present invention, radical crosslinking uniformly occurs between the polymer molecules. Uniformity of radical crosslinking can be assessed by the water absorbing and swelling properties of the product and the feeling upon touch on the hydrogel formed as a result of the water absorption of the product. The degree of crosslinking of the polymer can be freely regulated by varying the amount of the initiator, the amount of water and other conditions.

The water absorbent polymer-coated article according to the present invention is excellent in uniformity with respect to water absorption and bonding strength between the substrate and the hydrogel as compared with the conventional products produced by spreading a polymer powder. It can be safely and advantageously utilized as a disposable diaper, sanitary napkin, surgical pad, surgical sheet, paper towel or the like. Applications of the article according to the present invention are also found in a wall material for dew condensation prevention, a water absorbent non-woven fabric and an improved absorbent cotton. In the present invention, a porous inorganic material such as pumice can also be employed as a substrate, and the product can be utilized as a water absorbent, water retaining material. For example, it may be blended with soil to give a water retaining effect suited for growth of plants.

The aqueous composition of the present invention, besides the above-mentioned advantages, has also the following interesting property. When the aqueous composition of the present invention is applied to an article comprising a substrate and, spread thereover, a powder of an acrylic polymer, a coat layer is formed so as to act as a strong binder between the powder and the substrate. With respect to this product, separation of a hydrogel formed by water absorption can be advantageously avoided.

The present invention will be illustrated in more detail with reference to the following Examples, which should not be construed to be limiting the scope of the present invention. The parts and percents are by weight unless otherwise indicated.

EXAMPLE 1

To a solution made by dissolving 32 parts of sodium hydroxide (purity: 93%) in 144 parts of water were added 72 parts of acrylic acid and 0.1 part of potassium persulfate to prepare an aqueous solution. The solution had an acrylic acid salt concentration of 35%, 75% of the entire amount of the acrylic acid had been converted to its sodium salt. The obtained aqueous solution was stirred in nitrogen atmosphere while maintaining the temperature of the solution within a range of 50° to 55° C. to effect polymerization. The polymerization was continued for 3 hours to obtain a highly viscous aqueous polymer solution.

An aliquot of the solution was collected and evaporated to dryness under reduced pressure to obtain a polymer. The obtained polymer was weighed to determine the concentration of the aqueous polymer solution. As a result, the solution was found to have a polymer concentration of 35%. This indicated that the polymerization had proceeded almost completely.

To 20 parts of the aqueous polymer solution was added 0.14 part of potassium persulfate, which corresponds to 2% of the polymer, to obtain a homogeneous solution. The obtained solution was put into a vessel to form a layer of the solution having a thickness of about 5 mm. The vessel was put in a dryer maintained at a temperature of 130° C. and dried for 5 hours to obtain a solid product in the form of a sheet. The solid product was pulverized into a powdery product. The powdery product was sifted with a sieve to obtain a powdery product having a particle diameter of 48 to 200 mesh (Tyler).

0.5 g of the obtained powdery product was separately put in 1000 ml of pure water and 100 ml of 0.9% saline solution (physiological saline solution), and 30 minutes later the formed hydrogel was filtered with a 80-mesh metal sieve and subjected to weighing. As a result, it was found that the absorbency of the polymer was 45 g per g of the polymer for 0.9 g saline solution and 490 g per g of the polymer for pure water.

The hydrogel was not sticky and had a comfortable touch.

EXAMPLE 2

The aqueous polymer solution prepared in Example 1 was heated and concentrated to obtain a gel-like composition having a concentration of 48%. The concentration was determined by drying the composition and weighing the resulting dried solid.

To 20 parts of this composition was added 0.08 part of ammonium persulfate, which corresponds to 0.83% of the polymer and the resulting mixture was kneaded in a kneader to dissolve the ammonium persulfate homogeneously into the composition. The obtained mixture was formed into a sheet having a thickness of about 3 mm, put in a dryer maintained at a temperature of 130° C. and dried for 3 hours to obtain a solid polymer. The polymer was pulverized into a powdery product. The powdery product was sifted with a sieve to obtain a powdery product having a particle diameter 48 to 200 mesh (Tyler). The absorbency of the powdery product was measured by the method as described in Example 1. As a result, it was found that the absorbency of the powdery product was 51 g/g for 0.9% saline solution and 540 g/g for pure water.

EXAMPLE 3

To a solution made by dissolving 30 parts of sodium hydroxide in 192 parts of water were added 64.8 parts of acrylic acid and 7.1 parts of acrylamide to obtain an aqueous solution. To the aqueous solution was added 0.1 part of potassium persulfate to prepare an aqueous solution. The solution had a concentration of 30%. 78% of the entire amount of the acrylic acid had been converted to its sodium salt. The solution was stirred in nitrogen atmosphere while maintaining the temperature within a range of 50° to 55° C. to effect polymerization. The polymerization was continued for 3 hours to obtain a highly viscous aqueous polymer solution.

The aqueous polymer solution was heated to concentrate the solution. As a result, a gel-like composition having a concentration of 50% was obtained. To 20 parts of the composition was added 0.08 part of potassium persulfate, which corresponds to 0.8% of the polymer. The obtained mixture was kneaded in a kneader to dissolve potassium persulfate homogeneously into the composition. The mixture was subjected to the same treatment as described in Example 1 to obtain a dried powdery product having a particle diameter of 48 to 200 mesh (Tyler). The absorbency of the obtained powdery product was measured by the method described in Example 1. As a result, it was found that the absorbency of the powdery product per g of the polymer was 42 g for 0.9% saline solution and 430 g for pure water.

EXAMPLE 4

To a solution made by dissolving 33.5 parts of sodium hydroxide (purity: 93%) in 113 parts of water were added 72 parts of acrylic acid to obtain an aqueous solution. To the aqueous solution was added 0.1 part of potassium persulfate to prepare an aqueous solution. The solution had a concentration of 40%. 78% of the entire acrylic acid had been converted to its sodium salt. The obtained solution was poured into a vessel to form a layer of the solution having a thickness of about 2 cm and heated in nitrogen atmosphere. The polymerization reaction was initiated when the temperature of the solution reached about 50° C. The polymerization reaction was continued for about 10 min with vigorous generation of steam. A portion of the resulting product was collected, dried and subjected to weighing. From the weight of the dried polymer, the water content of the product was found to be 48%. The product was a rubber-like substance and had a portion insoluble to water.

To 20 parts of the product was added 0.052 part of potassium persulfate, which corresponds to 0.5% of the polymer. The resulting mixture was kneaded in a kneader to dissolve potassium persulfate homogeneously into the product. The kneaded mixture was formed into a sheet having a thickness of about 3 mm and dried in a dryer maintained at a temperature of 140° C. for 3 hours to obtain a solid polymer. The polymer was pulverized into a powdery product. The powdery product was sifted with a sieve to obtain a powdery product having a particle diameter of 48 to 200 mesh (Tyler). The absorbency of the powdery product was measured by the method as described in Example 1. As a result, it was found that the absorbency of the powdery product per g of the polymer was 62 g for 0.9% saline solution and 680 g for pure water.

EXAMPLE 5

To a solution made by dissolving 34 parts of sodium hydroxide (purity: 93%) in 340 parts of water were added 72 parts of acrylic acid and 0.1 part of potassium persulfate to prepare an aqueous solution. The solution had an acrylic acid salt concentration of 20%. 80% of the entire amount of the acrylic acid had been converted to its sodium salt.

The obtained aqueous solution was stirred in nitrogen atmosphere while maintaining the temperature of the solution within a range of 55° to 60° C. to effect polymerization. The polymerization was continued for 4 hours to obtain a highly viscous aqueous polymer solution. The aqueous polymer solution was diluted with the equal volume of water to obtain an aqueous solution having a polymer concentration of 10%. The viscosity of the obtained solution was 320 centipoises. Further, the aqueous polymer solution was diluted with a mixed solvent of water and methanol (1:1 by volume) to obtain a solution having a polymer concentration of 10%. The viscosity of the obtained solution was 240 centipoise.

In the solution obtained by diluting the aqueous polymer solution with a mixed solvent of water and methanol was dissolved potassium persulfate in an amount of 3% based on the amount of the polymer. 10 parts of an absorbent cotton were uniformly impregnated with this solution to obtain an impregnation mixture. From the weight increase of the absorbent cotton, the amount of the solution which had permeated into the absorbent cotton was found to be 18 parts. This amount corresponds to 1.8 part of the polymer. The obtained impregnation mixture was concentrated at a temperature of 60° C. until the weight of the mixture was reduced to 16 parts. Then, the impregnation mixture was held between a pair of hot plates each having a temperature of 150° C. and dried for 30 min to obtain a product. The weight of the product was 11.9 parts.

1 g of the product was put in 100 ml of water. After 60 min, the product was filtered off with an 80 mesh metal sieve, lightly squeezed and weighed. The weight of the product was 52 g. On the other hand, 1 g of an untreated absorbent cotton was put in water and subjected to the treatment as described above. As a result, it was found that the weight of the untreated absorbent cotton which had absorbed water was 15 g. The water absorbency of the product per g of the polymer was 260 g as calculated on the basis of the difference between the weight after water absorption of the product and that of the untreated absorbent cotton. Further, the above-mentioned product and untreated absorbent cotton both after water absorption were separately compressed to discharge water. The amounts of water discharged by the product and the untreated absorbent cotton were compared. As a result, it was found that the product (absorbent cotton impregnated with the polymer) had a remarkably high water-retaining capabilities as compared with the untreated absorbent cotton.

EXAMPLE 6

10 parts of a fibrous pulp web were uniformly impregnated with the aqueous polymer solution having a polymer concentration of 10% prepared in Example 5 to obtain an impregnation mixture. The amount of the solution which had permeated into the web was 26 parts as calculated on the basis of the difference between the weight of the web after the impregnation and that before the impregnation. This amount corresponds to 2.6 parts of the polymer. The impregnation mixture was concentrated in a dryer having a temperature of 60° C. until the weight of the mixture was reduced to 18 parts. Then, the mixture was dried in substantially the same manner as in Example 5 to obtain a product. After drying, the weight of the impregnation mixture was 12.6 parts.

1 g of the thus obtained product was subjected to the measurement of the water absorbency by the method as described in Example 5. As a result, the weight of the product which had absorbed water was found to be 59 parts. On the other hand, the untreated fibrous pulp web was also subjected to the measurement of the water absorbency by the method as described in Example 5. As a result, the weight of the untreated fibrous pulp web which had absorbed water was 10 g. The water absorbency of the product per g of the polymer was 250 g as calculated on the basis of the difference between the weights after water absorption of the product and that of the untreated fibrous pulp web.

EXAMPLE 7

To a solution made by dissolving 33.6 parts of sodium hydroxide (purity: 93%) in 247 parts of water were added 72 parts of acrylic acid and 0.1 part of potassium persulfate to prepare an aqueous solution. The solution had an acrylic acid salt concentration of 25%. 78% of the entire amount of the acrylic acid had been converted to its sodium salt.

The solution was subjected to polymerization by the same method as described in Example 5 to obtain a highly viscous aqueous polymer solution. The aqueous polymer solution was diluted two-fold with a mixed solvent of water and methanol (1:1 by volume) to prepare a polymer solution having a polymer concentration of 12.4%. The concentration was determined on the basis of the weight of polymer brought to dryness by evaporation. In the solution was dissolved potassium persulfate in an amount corresponding to 2.5% of the polymer.

1.5 parts of a fine powder of the water absorbent polymer prepared in Example 1 (absorbency for pure water: 490 g per g of the polymer) was uniformly spread over a fibrous pulp web. Further, the fibrous pulp web was uniformly impregnated with 15 parts of the above-obtained polymer solution to obtain an impregnation mixture. The impregnation mixture was concentrated in a dryer maintained at a temperature of 60° C. until the weight of the mixture was reduced to 16 parts. Then, the impregnation mixture was dried in substantially the same manner as in Example 5 to obtain a product. The weight of the product was 13.5 parts.

1 g of the thus obtained product was subjected to the measurement of the water absorbency by the method as described in Examples 5. As a result, it was found that the weight of the product which had absorbed water was 83 g. This indicates that the water absorbency of the product per g of the polymer is about 300 g.

EXAMPLE 8

10 parts of porous glass beads having an average particle diameter of 4 mm was uniformly impregnated with 5 parts of the polymer solution prepared in Example 7 to obtain an impregnation mixture. The impregnation mixture was concentrated in a dryer maintained at a temperature of 60° C. until the weight of the mixture was reduced to 12 parts. Then the impregnation mixture was dried in a superheated steam for 30 min to obtain a product. The weight of the product was 10.6 parts.

1 g of the thus obtained product was subjected to the measurement of the water absorbency by the method described in Example 5. As a result, it was found that the weight of the product which had absorbed water was 13.5 parts.

What is claimed is:

1. An aqueous composition consisting essentially of at least about 10% by weight of water, a polymer dissolved or swollen in said water and a persulfate radical initiator substantially dissolved in said water, said polymer having at least 70% by weight, based on the total weight of said polymer, of acrylic acid monomeric units, 60 to 90% of the carboxyl groups of said monomeric units being in the form of an alkali metal salt, with the balance of the polymer comprising monomeric units of methacrylic acid, maleic anhydride, fumaric acid, acrylamide, or methacrylamide, said initiator being adapted to decompose at a temperature of from about 40° to about 180° C. and act on said polymer to crosslink said polymer.

2. A composition according to claim 1, wherein said polymer is a water soluble polymer.

3. A composition according to claim 1, wherein said initiator is present in an amount of from 0.01 to 10% by weight based on said polymer.

4. A composition according to claim 3, wherein said initiator is present in an amount of from 0.1 to 5% by weight based on said polymer.

5. A composition according to claim 4, wherein said initiator is present in an amount of from 0.5 to 3% by weight based on said polymer.

6. A composition according to claim 1, wherein said water is present in an amount of at least about 20% by weight based on said composition.

7. A composition according to claim 6, wherein said water is present in an amount of from about 20% to about 60% by weight based on said composition.

8. A composition according to claim 6, which further comprises a volatile, water soluble organic solvent.

9. A composition according to claim 8, wherein said organic solvent is an alcohol or a ketone compound.

10. A composition according to claim 8, wherein said solvent is present in an amount of from 0.1 to 5 in terms of the volume ratio of said solvent to water.

11. A method of producing a water absorbent crosslinked polymer, which comprises the steps of:
    (1) providing an aqueous mixture consisting essentially of water and a polymer dissolved or swollen in said water, said polymer having at least 70% by weight, based on the total weight of said polymer, of acrylic acid monomeric units 60 to 90% of the carboxyl groups of said monomeric units being in the form of an alkali metal salt;
    (2) adding a water soluble persulfate radical initiator, said initiator being adapted to decompose at a temperature of from about 40° to about 180° C. and act on said polymer to crosslink said polymer, to said mixture in an amount sufficient to crosslink said polymer and in such an amount that said water substantially dissolves said initiator therein thereby to obtain an aqueous composition; and (3) heating said aqueous composition at a temperature of from about 40° to about 180° C.

12. A method according to claim 11, wherein said polymer is a water soluble polymer.

13. A method according to claim 11, wherein the aqueous composition has a water content of at least about 10% by weight.

14. A method according to claim 13, wherein the aqueous composition has a water content of at least about 20% by weight.

15. A method according to claim 14, wherein the aqueous composition has a water content of about 20 to about 60% by weight.

16. A composition according to claim 2, wherein said polymer consists of acrylic acid monomeric units, 60 to 90% of the carboxyl groups of the monomeric units being in the form of an alkali metal salt.

* * * * *